United States Patent [19]

Schoolnik et al.

[11] Patent Number: 4,622,223
[45] Date of Patent: Nov. 11, 1986

[54] BROAD SPECTRUM VACCINE AGAINST GONORRHEA

[75] Inventors: Gary K. Schoolnik, Palo Alto; Jonathan Rothbard, San Francisco, both of Calif.

[73] Assignee: The Board of Trustees for the Leland Stanford University, Palo Alto, Calif.

[21] Appl. No.: 759,123

[22] Filed: Jul. 25, 1985

Related U.S. Application Data

[63] Continuation-in-part of Ser. No. 623,178, Jun. 21, 1984, Pat. No. 4,584,195.

[51] Int. Cl.⁴ .................. A61K 39/095; C07K 7/06; C07K 7/08
[52] U.S. Cl. .................................... 424/92; 424/88; 530/326; 530/327; 530/328
[58] Field of Search .................. 260/112.5 R; 424/88, 424/92

[56] References Cited

U.S. PATENT DOCUMENTS 4,443,431 4/1984 Buchanan et al. .................. 424/92

OTHER PUBLICATIONS

Chemical Abstracts, vol. 98, Abstract No. 213829n, 1983.
Chemical Abstracts, vol. 101, Abstract No. 125160n, 1984.

*Primary Examiner*—Blondel Hazel
*Attorney, Agent, or Firm*—Ciotti & Murashige

[57] ABSTRACT

Vaccines comprising peptide sequences corresponding to immunorecessive determinants in gonorrhea pilus protein are disclosed. The vaccines are effective in protecting human subjects against infection by a wide range of gonorrhea strains by raising antibodies which interfere with the colonization of the epithelium by the infecting bacteria or which enhance phagocytosis.

16 Claims, 1 Drawing Figure

MePhe - Thr - Leu - Ile - Glu - Leu - Met - Ile - Val - Ile - Ala - Ile - Val - Gly - Ile - Leu - Ala - Ala - Val - Ala - 20
Leu - Pro - Ala - Tyr - Gln - Asp - Tyr - Thr - Ala - Arg - Ala - Gln - Val - Ser - Glu - Ala - Ile - Leu - Leu - Ala - 40
21 – 35
                                                              48 – 60
Glu - Gly - Gln - Lys - Ser - Ala - Val - Thr - Glu - Tyr - Tyr - Leu - Asn - His - Gly - Lys - Trp - Pro - Glu - Asn - 60
41 – 50
                                              69 – 84
Asn - Thr - Ser - Ala - Gly - Val - Ala - Ser - Pro - Pro - Ser - Asp - Ile - Lys - Gly - Lys - Tyr - Val - Lys - Glu - 80
Val - Glu - Val - Lys - Asn - Gly - Val - Val - Thr - Ala - Thr - Met - Leu - Ser - Ser - Gly - Val - Asn - Asn - Glu - 100
                                                                                    107 – 121
Ile - Lys - Gly - Lys - Lys - Leu - Ser - Leu - Trp - Ala - Arg - Arg - Glu - Asn - Gly - Ser - Val - Lys - Trp - Phe - 120
                                                                                              135 – 151
Cys - Gly - Gln - Pro - Val - Thr - Arg - Thr - Asp - Asp - Thr - Val - Ala - Asp - Ala - Lys - Asp - Gly - Lys - 140
                                                                                  151 – 159
Glu - Ile - Asp - Thr - Lys - His - Leu - Pro - Ser - Thr - Cys - Arg - Asp - Lys - Ala - Ser - Asp - Ala - Lys - (COOH)

FIG. I

BROAD SPECTRUM VACCINE AGAINST GONORRHEA

CROSS-REFERENCE TO RELATED APPLICATION

This application is a continuation-in-part of copending U.S. patent application Ser. No. 623,178, filed 21 June 21, 1984, now U.S. Pat. No. 4,584,195.

TECHNICAL FIELD

This invention relates to immunization of humans against gonorrheal infection. In particular, it relates to vaccines useful in protecting humans against a broad spectrum of gonococcus strains.

BACKGROUND ART

Gonorrhea is a well known, sexually transmitted disease which produces acute suppuration of the mucous membranes of the genital urinary tract and the eye followed by chronic inflammation and fibrosis. It is caused by a gram negative group of cocci *Neisseria gonorrhoeae* (gonococcus). A single strain of this species is an isolate from a single host (patient) at a particular site. There are, therefore, multitudinous strains of *N. gonorrhoeae*, each of which has characteristic antigenic determinants assocated with the pili, a fact which renders both diagnosis and immunization difficult. The incidence of the disease has markedly increased since 1955, and has been complicated by the appearance of penicillin resistant strains harboring β-lactamase encoding plasmids, which were first reported in 1976. The infectivity of the organism is extremely high, and it has been estimated that a single sexual encounter with an infected partner results in a 20–30% probability of acquiring the disease. If left untreated, relapses are to be expected, as resistance to re-infection does not appear to develop.

The course of the disease involves colonization of the mucous membranes by the bacterium, a process which is mediated by the attachment of the colonizing cell to the surface membrane by means of filamentous structures called pili associated with its cell wall. After attachment, the gonococcus is passed through the epithelium to the submucosal space where it is capable of causing inflammation and fibrosis. The attachment of the gonococci to the epithelial surface can be blocked by anti-pilus antibody.

In addition to blocking cell attachment, antibodies raised against pilus protein are also opsonic—i.e., they mediate the killing of the invading bacteria by the phagocytes in the blood. However, the use of pilus immunogens as vaccines has been rendered impractical by the lack of cross-reactivity among strains.

The lack of cross-reactivity of antibodies raised against pili of various strains has been shown not to be absolute. (Brinton, C. C. Jr. et al, *Immunobiology of Neisseria Gonorrheae* (1978) American Society for Microbiology, Washington, D.C., p. 155). Also, the nature of the pilus protein has been studied. The filamentous portion consists of a polymeric form of a monomeric polypeptide, pilin, and the complete amino acid sequence of the pilin isolated from the transparent colonial variant (Tr) of strain MS11 and a partial sequence of R10 (Tr) pilin have been determined (Schoolnik, G. K. et al, *J. Exp. Med.* (1984) 159:1351). It has also been shown that when the pilin associated with either of these two strains is treated with cyanogen bromide, two immunologically important fragments CNBr-2, residues 9–92, and CNBr-3, residues 93–159, are generated which appear to represent immunologically different portions of the molecule. CNBr-3 is apparently antigenically variable and immunodominant; CNBr-2 apparently contains a conserved receptor-binding region and is immunorecessive. (Schoolnik, G. K. et al, *Prog. Allergy* (1983) 33:314). None of the foregoing work has resulted in a material which can serve as a effective vaccine against all strains of *N. gonorrhoeae*. By providing an immunogenic form of an antigenic determinant capable of eliciting antibodies reactive against all strains either by inhibiting attachment, or by encouraging phagocytosis or both, protection would be provided against gonnorheal infection. This is the accomplishment of the present invention.

DISCLOSURE OF THE INVENTION

It has now been found that certain portions of the amino acid sequence associated with the pilus protein are capable, when made immunogenic, of eliciting antibodies which are capable not only of reacting against pili of a wide spectrum of gonococcal strains, but also of either preventing the adherence of these strains to epithelial cells or aiding their destruction by phagocytes, or both. Some of the peptide sequences are those associated with the immunorecessive, receptor-binding portion of the conserved region of the pilin, and reside in the CNBr-2 fragment. Others reside in the CNBr-3 portion. When these antigenically reactive peptide sequences are bound to a carrier protein so as to confer immunogenicity upon them, they can be used as a vaccine to protect a person injected or otherwise administered the vaccine against gonorrhea. Gonorrhea appears to infect only human beings and not other mammals, and thus an animal model of the disease does not exist, nor is there a need for a vaccine to protect other animals against the disease.

Accordingly, in one aspect, this invention relates to a vaccine effective against gonorrhea infection in humans which comprises an effectively protective amount of a peptide of an antigenic, conserved sequence substantially equivalent to the amino acid sequence represented by residues 21–35, 41–50, 48–60, 69–84, 107–121, 135–151 or 151–159 of *N. gonorrhoeae* MS11(Tr) linked to a substantially antigenically neutral carrier protein.

In other aspects, the invention relates to these amino acid sequences with additional residues at the carboxy termini to facilitate linkage to the carrier protein in the correct orientation, and to the conjugation products resulting. It also, in other aspects, relates to the foregoing peptide sequences in substantially pure form, and to methods for protecting human beings against gonorrheal infection using the vaccines of the invention.

BRIEF DESCRIPTION OF THE DRAWINGS

FIG. 1 shows the amino acid sequence of N-methyl(-phenylala) MS11 pilin, and the regions representing the proteins of the invention.

MODES OF CARRYING OUT THE INVENTION

A. Definitions

As used herein, "substantially equivalent to" in characterizing a peptide sequence means that the substantial equivalent is capable of carrying out the same antigenic function and mediating the immunologic function of the referenced sequence. In general, the sequence of amino acids in the substantially equivalent peptide and the referenced peptide will be identical, however, as is well understood, it may be possible to substitute or modify a small number of these residues without appreciable impact on the performance of the resulting polypeptide. Means are now understood in the art for deleting, adding, or modifying individual amino acid residues either directly or by altering their coding sequences, and modifications so performed which result in polypeptide sequences of equivalent performance generate peptides which are "substantially equivalent".

"Peptide", "polypeptide", and "protein" are used interchangeably, and refer to amino acid sequences of a variety of lengths, either in their neutral (uncharged) forms or in forms which are salts, and either free of modifications such as glycosylation, side chain oxidation, or phosphorylation or containing these modifications. It is well understood in the art that amino acid sequences contain acidic and basic groups, and that the particular ionization state exhibited by the peptide is dependent on the pH of the surrounding medium when the protein is in solution, or that of the medium from which it was obtained if the protein is in solid form. Also included in the definition are proteins modified by additional substituents attached to the amino acid side chains, such as glycosyl units, lipids, or inorganic ions such as phosphates, as well as modifications relating to chemical conversions of the chains, such as oxidation of sulfhydryl groups. Thus, "peptide" or its equivalent terms is intended to include the appropriate amino acid sequence referenced, subject to those of the foregoing modifications which do not destroy its functionality.

"Substantially antigenically neutral carrier" refers to a material to which the peptides of the invention may be attached to render them immunogenic, but which does not itself elicit antibodies which will be detrimental to the host, or contain antigenic sites which interfere with the antigenic function of the invention peptides. In the illustration below, as rabbits were used as a source of antibody, bovine serum albumin (BSA) could be used. For human use, however, carriers would be limited to proteins which do not raise antibodies to materials commonly and non-pathogenically encountered by humans. For example, the somatic "Protein I" of the gonococcus itself could be used, as could tetanus toxoid protein. The use of other carriers is not precluded; however, these are the most convenient forms of serologically compatible carriers and are, at the present time, the most conveniently used representatives of this class.

B. General Description

B.1. Gonococal Pili and the Antigenic Sequences

Pilin isolated from *N. gonorrhoeae* strain MS11(Tr) has been shown to be a 159 amino acid peptide having two cysteine residues, at positions 121 and 151, which are joined by a disulfide link to create a loop in the chain between these two positions. (See FIG. 1.) The presence of methionine residues at positions 7 and 92 gives rise to three cyanogen bromide fragments two of which have been used extensively in immunological studies; i.e., CNBr-1 (residues 1–7); CNBr-2 (residues 8–92) and CNBr3 (residues 93–159 ). The amino acid sequence of CNBr-2 contains two domains represented by approximately positions 41–50 and 69–84, which are hydrophilic and which can be shown by computer analysis of the sequence to contain beta turns, thus indicating their proximity to the surface of the protein. The amino acid sequences in these regions represent two of the immunogenic portions of the vaccines of the invention which generate adherence-blocking antibodies. The antibodies generated in response to these positions are also opsonic. In addition, peptides substantially equivalent to positions 48–60 and 135–151 function, when linked to carriers, are immunogens capable of raising high-titer opsonic antibodies; peptides substantially equivalent to positions 21–35, 107–121 and 151–159 also raise opsonic antibodies having somewhat lower titers. The seven peptides capable of raising opsonic antibodies are indicated in FIG. 1.

B.2. Linkers

Because the peptide sequences above are considered too small to be immunogenic, they have been linked to carrier substances in order to confer this property upon them. Any method of creating such linkages known in the art may be used.

Linkages can be formed in a variety of ways. For example, there are a large number of heterobifunctional agents which generate a disulfide link at one functional group end and a peptide link at the other, and these have been used extensively. The most popular of these is N-succidimidyl-3-(2-pyridyldithio) proprionate (SPDP). This reagent creates a disulfide linkage between itself and a cysteine residue in one protein and an amide linkage through the ε amino on a lysine, or other free amino group in the other. A variety of such disulfide/amide forming agents are known. See for example *Immun. Rev.* (1982) 62:185. Other bifunctional coupling agents form a thioether rather than a disulfide linkage. Many of these thioether forming agents are commercially available and include reactive esters of 6-maleimidocaproic acid, 2 bromoacetic acid, 2-iodoacetic acid, 4-(N-maleimido-methyl) cyclohexane-1-carboxylic acid and the like. The carboxyl groups can be activated by combining them with succinimide or 1-hydroxy-2-nitro-4-sulfonic acid, sodium salt. The particularly preferred coupling agent for the method of this invention is succinimmidyl 4-(N-maleimido-methyl) cyclohexane-1-carobxylate (SMCC) obtained from Pierce Company, Rockford, Illinois. The foregoing list is not meant to be exhaustive, and modifications of the named compounds can clearly be used.

B.3. Methods of Preparation of the Immunogenic Active Ingredient

The antigenic peptides of the invention can be prepared in a number of conventional ways. Because they are short sequences, they can be prepared by chemical synthesis using standard means. Particularly convenient are solid phase techniques (see for example Erikson, B. W. et al, *The Proteins* (1976) v. 2, Academic Press, New York, p. 255). Indeed, automated solid phase synthesizers are commerically available, as are the reagents required for their use. Thus, not only is it possible to mimic the sequence of amino acids in the designated positions of the MS11 pilin, modifications in the sequence can easily be made by substitution, addition or omission of appropriate residues. Particularly convenient modifications, as set forth above, include the addition of a cysteine residue at the carboxy terminus to provide a sulfhydryl group for convenient linkage to the carrier protein. In addition, spacer elements, such as an additional glycine residue may be incorporated into the sequence between the linking amino acid at the C-terminus and the remainder of the peptide.

Also because the desired sequences are relatively short, recombinant techniques to produce these peptides are particularly appealing. The coding sequence for peptides of this length can easily be synthesized by chemical techniques, for example, the phosphotriester method of Matteucci, M. et al, *J Am Chem Soc* (1981) 103:3185. Of course, by chemically synthesizing the coding sequence, any desired modification can be made simply by substituting the appropriate bases for those encoding the native peptide sequence. The coding sequence can then be provided with appropriate linkers and ligated into expression vectors now commonly available in the art, and the resulting vectors used to transform suitable hosts to produce the desired protein.

A number of such vectors and suitable host systems are now available. For example promoter sequences compatible with bacterial hosts are provided in plasmids containing convenient restriction sites for insertion of the desired coding sequence. Typical of such vector plasmids are, for example, pUC8, and pUC13 available from Messing, J., at the University of Minnesota; (see, e.g., Messing, et al, *Nucleic Acids Res* (1981) 9:309) or pBR322, available from New England Biolabs. Suitable promoters include, for example, the $\beta$-lactamase (penicillinase) and lactose (lac) promoter systems (Chang, et al, *Nature* (1977) 198:1056 and the tryptophan (trp) promoter system (Goeddel, D., et al, *Nucleic Acids Rec* (1980) 8:4057)). The resulting expression vectors are transformed into suitable bacterial hosts using the calcium chloride method described by Cohen, S. N., et al, *Proc Natl Acad Sci* USA (1972) 69:2110. Successful transformants may produce the desired polypeptide fragments at higher levels than those found in strains normally producing the intact pili. Of course, yeast or mammalian cell hosts may also be used, employing suitable vectors and control sequences.

Finally, these sequences can also be prepared by isolation of native pilin and hydrolysis of the peptides obtained. However, this method is the least practical, as large amounts of unwanted protein must be eliminated from the original preparation.

The antigenic peptide sequence containing suitable modification to provide for linkage can then be provided with a suitable antigenically neutral carrier using any of a variety of linking agents as set forth above. Suitable carriers include the aforementioned Protein I and tetanus toxoid and these can be linked to the antigenic peptide through, for example, bifunctional linkers providing thioether or disulfide links and amide linkages. The conditions of such linkage of course depend on the nature of the linker used, and are well understood in the art.

B.4. Vaccine Preparation

Prepration of vaccines which contain peptide sequences as active ingredients is also well understood in the art. Typically, such vaccines are prepared as injectables, either as liquid solutions or suspensions; solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccine. The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides; such suppositories may be formed from mixtures containing the active ingredient in the range of 0.5% to 10%, preferably 1%-2%. Oral formulations include such normally employed excipients as, for example, pharmaceutical grades of manitol, lactose, starch, magnesium stearate, sodium saccharine, cellulose, magnesium carbonate and the like. These compositions take the form of solutions, suspensions, tablets, pills, capsules, sustained release formulations or powders and contain 10%-95% of active ingredient, preferably 25%-70%.

The proteins may be formulated into the vaccine as neutral or salt forms. Pharmaceutically acceptable salts, include the acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, capacity of the subject's immune system to synthesize antibodies, and the degree of protection desired. Precise amounts of active ingredient required to be administered depend on the judgment of the practitioner and are peculiar to each individual. However, suitable dosage ranges are of the order of several hundred micrograms active ingredient per individual. Suitable regimes for initial administration and booster shots are also variable, but are typified by an initial administration followed in one or two week intervals by a subsequent injection or other administration.

C. EXAMPLES

The following are intended to illustrate but not to limit the invention.

C.1. Preparation of Active Ingredients

The peptide substantially equivalent to positions 41–50, Glu-Gly-Gln-Lys-Ser-Ala-Val-Thr-Glu-Tyr, was synthesized on a commercial Beckman Model 990B Peptide Synthesizer using commerically available amino acid polystyrene resins and t-Boc protected amino acids (Peninsula Laboratories, Belmont, California), with the following side chain protecting groups: O-benzyl esters for Asp, Glu, Thr, and Ser; tosyl for Arg and His; p-methoxybenzyl for Cys, o-chlorobenzyloxycarbonyl for Lys, and 2, 6-dichlorobenzyl for Tyr. Coupling was performed using a 2.5 molar excess of t-Boc amino acid and dicyclohexylcarbodiimide (DCC) over resin bound amino acid. In the case of Asn and Gln, a 2.5 molar excess of the amino acid, DCC, and N-hydroxytriazole was used. All couplings were more than 99% complete, as determined by the reaction of the resin with ninhydrin. The peptides were simultaneously deprotected and removed from the resin by treatment with anhydrous HF in the presence of anisole, dimethylsulfide, and indole. The peptides were separated from the various organic side products by extraction with ether, isolated from the resin by raction with 5% acetic acid and then lyophilized. The purity of the crude product was determined by HPLC on a C-18 reverse phase column (Merck, Darmstadt, Germany) and by amino acid analysis. The peptide was determined to be more than 90% pure.

In a similar manner the following peptides were prepared:

For additional peptides representing positions 41-50:
Glu-Gly-Gln-Lys-Ser-Ala-Val-Thr-Glu-Tyr-Cys;
Glu-Gly-Gln-Lys-Ser-Ala-Val-Thr-Glu-Tyr-Gly-Cys.

For positions 21-35
Leu-Pro-Ala-Tyr-Gln-Asp-Tyr-Thr-Ala-Arg-Ala-Gln-Val-Ser-Glu;
Leu-Pro-Ala-Tyr-Gln-Asp-Tyr-Thr-Ala-Arg-Ala-Gln-Val-Ser-Glu-Cys; and
Leu-Pro-Ala-Tyr-Gln-Asp-Tyr-Thr-Ala-Arg-Ala-Gln-Val-Ser-Glu-Gly-Cys.

For positions 48-60:
Thr-Glu-Tyr-Tyr-Leu-Asn-His-Gly-Lys-Trp-Pro-Glu-Asn;
Thr-Glu-Tyr-Tyr-Leu-Asn-His-Gly-Lys-Trp-Pro-Glu-Asn-Cys; and
Thr-Glu-Tyr-Tyr-Leu-Asn-His-Gly-Lys-Trp-Pro-Glu-Asn-Gly-Cys.

For positions 69-84:
Pro-Pro-Ser-Asp-Ile-Lys-Gly-Lys-Tyr-Val-Lys-Glu-Val-Glu-Val-Lys;
Pro-Pro-Ser-Asp-Ile-Lys-Gly-Lys-Tyr-Val-Lys-Glu-Val-Glu-Val-Lys-Cys; and
Pro-Pro-Ser-Asp-Ile-Lys-Gly-Lys-Tyr-Val-Lys-Glu-Val-Glu-Val-Lys-Gly-Cys.

For positions 107-121:
Ser-Leu-Trp-Ala-Arg-Arg-Glu-Asn-Gly-Ser-Val-Lys-Trp-Phe-Cys; and For positions 135-151:
Asp-Ala-Lys-Asp-Gly-Lys-Glu-Ile-Asp-Thr-Lys-His-Leu-Pro-Ser-Thr-Cys;

For positions 151-159:
Cys-Arg-Asp-Lys-Ala-Sar-Asp-Ala-Lys;
Arg-Asp-Lys-Ala-Ser-Asp-Ala-Lys-Cys; and
Arg-Asp-Lys-Ala-Ser-Asp-Ala-Lys-Gly-Cys.

C.2. Linkage to Carrier Protein

The peptides from paragraph C.1. which contain a C-N-terminal Cys residue are linked to bovine serum albumin using succinimidyl 4-(N-maleimidomethyl) cyclohexane-1-carboxylate (SMCC) (Pierce, Rockford, Ill.) as described by Yoshitake, S. et al, *Eur J. Biochem.* (1979) 101: 395. Briefly, 10 mg BSA is dissolved in 2 ml phosphate buffered saline (PBS), pH 7.4 and combined with 5 mg of SMCC in 0.5 ml of dimethylformamide. After one hour at room temperature, the conjugate was separated from unreacted SMCC by gel filtration on G-25 in 0.1 M phosphate, pH 6.0.

The peptide Glu-Gly-Gln-Lys-Ser-Ala-Val-Thr-Glu-Tyr-Cys was dissolved in 0.1M borate, pH 9.1 and reduced with NaBH$_4$ (0.1 ml of 0.1M stock). After five minutes, the pH of the borate solution was lowered to 1 with 1M HCl to remove excess NaBH$_4$ and then raised to pH 6 with 1M NaOH, and combined with the linker-BSA conjugate. After incubating at room temperature for an additional hour, the peptide-linker-BSA conjugate was desalted on a G-25 column in 0.1M NH$_4$HCO$_3$. The degree of conjugation was quantitated by comparing the amino acid composition of the BSA before and after reaction with the peptide. The conjugate contained approximately 15-25 peptides per molecule of BSA.

In a similar manner, the other C-terminal Cys containing peptides of paragraph C.1. were conjugated with BSA.

C.3. Confirmation of Antigenicity of Peptide Conjugates

Several procedures were employed to confirm that the peptide conjugates representing positions 41-50 and 69-84 had the ability to bind specifically to antibodies against gonococcal pili. The antibodies tested were raised against purified whole pili derived from R10 or MS11 or against CNBr2 and CNBr3 fragments thereof. The antibodies were raised in rabbits using standard techniques and were therefore polyclonal preparations. Assessment was done using RIA, ELISA, and by adsorption by peptide-carrier-sepharose conjugates.

For RIA and ELISA, 96 well plates were coated with 10 mg of the peptide BSA conjugate to be tested, washed, treated with serially diluted antiserum, washed, and then treated with reagent. For RIA, the reagent was 125I protein A (Amersham, Arlington Heights, Ill.). For ELISA, the reagent was goat anti-rabbit alkaline phosphatase conjugate (Cappel, Westchester, PA) followed by p-nitrophenyl phosphate. Radioactive wells (RIA) were cut from the plate and counted. For the ELISA the wells were read at 405 nm.

In the sepharose adsorption assay, the peptide-BSA conjugates were reacted with CNBr activated sepharose (Pharmacia, Piscataway, NJ) as described by Porath, J. et al, Meth Enzymol (1974) 34: 13. The antibody containing serum (1 ml) was exposed with 0.1 ml of the peptide-carrier-sepharose for 2 hours at room temperature, and the mixture separated by centrifugation. Supernatant was then assayed for the presence of antibody using a standard solid phase binding assay.

These assays showed a mixed response. The only anti-sera to which the peptide conjugates prepared in paragraph C.2 bound were those raised against the CNBr2 fragment of MS11 or R10. Conjugates containing antigenic peptides substantially similar both to protein 41-50 and to 69-84 bound to anti R10 CNBr2, only the 69-84 conjugate bound well to anti-MS11-CNBr2. Neither was responsive to antibodies against whole pili.

These results are consistent with the immunorescessive nature of these antigenic determinants. It would, indeed, be expected that immunogenic regions having the potential for generating antibodies of high cross reactivity would, in the context of species generating highly strain specific antibodies, be recessive.

C.4. Confirmation of Adherence Blocking Ability.

To test the ability of antibodies raised against the conjugated peptides of the invention to block adherence to target cells, an in vitro assay was used.

To obtain the target cells, epithelial cells derived from human endometrial cells were grown in monolayer tissue culture on cover slips.

An inoculum of piliated gonococcal strain F62 was pre-incubated with varying serum dilutions and transferred to a chamber containing the cultured cells. After 30 minutes of incubation, unbound bacteria were removed by repeated washings. The cover slip was strained using Giemsa and the number of adhering bacteria counted.

The results are shown in Table 1. "Pre" refers to a control serum, i.e., without immunization with the indicated peptide. "Post" refers to serum obtained from immunized animals.

To obtain the "post" immune serum, the peptide to be tested was conjugated to carrier and prepared as a vaccine in complete Freunds's adjuvant as follows: 500 μg of the conjugate in phosphate buffered saline (PBS) was emulsified with an equal volume of adjuvant. The vaccine was administered to 7 kg female New Zealand white rabbits by intramuscular or subcutaneous injection. Boosters were given after 6 weeks with similar vaccine and the animals were bled 10 days thereafter and the sera prepared for assay.

Serial dilutions of anti-sera prepared against the conjugates were heat-inactivated (56° C.×45 min), serially diluted in Hanks' salt solution and gelatine, and combined with equal volumes of the PMN's and bacteria. The reaction was allowed to proceed at 37° C. under continuous rotation (4 rev/min). After an incubation period of 15 min, phagocytosis was stopped instantly by bringing the reactants to 2° C. The bacteria-cell suspen-

TABLE 1

| Serum Dilution$^{-1}$ | Antisera Against: | | | | | |
|---|---|---|---|---|---|---|
| | 41–50 Conjugate | | 48–60 Conjugate | | 69–84 Conjugate | |
| | Pre | Post | Pre | Post | Pre | Post |
| 10 | 37.2 + 7.8* | 28 + 1.6 | 48.3 + 14.0 | 55.8 + 15.3 | 26.3 + 9.4 | 1.6 + 1.5 |
| 25 | 64.9 + 14.5 | 9.2 + 3.9 | N.D.+ | N.D. | 47.5 + 10.1 | 7.6 + 2.6 |
| 50 | 82.5 + 9.1 | 9.4 + 4.6 | N.D. | N.D. | 170.0 + 21.2 | 10.2 + 3.9 |
| 100 | N.D. | N.D. | N.D. | N.D. | 93.7 + 11.3 | 10.8 + 2.2 |

*Bacteria per cell ± S.D.
+N.D. - Not determined.

The results in Table 1 show that immune serum against the peptide conjugate substantially equivalent to MS11 pilin positions 69–84 was effective in blocking adherence to epithelial cells at all dilutions tested (at least 1:100), and that the antiserum raised against pilin positions 41–50 was comparably effective. A control using a peptide conjugate corresponding to positions 48–60 showed no ability to inhibit binding.

In summary, vaccines prepared from conjugates of peptides substantially equivalent to positions 41–50 or 69–84 of MS11 pili are protective against infection by virtue of their ability to raise antibodies which inhibit adherence of gonoccal pili derived from a broad spectrum of strains.

C.5. Confirmation of Opsonic Activity for Antibodies Generated by Conjugates of Invention Peptides Antibodies were raised as set forth in ¶C.4 by injecting the conjugates into rabbits. The resulting antisera were tested for opsonic behavior using a modification of the method of Cohn, Z. A., et al, *J Exp Med* (1959) 110:419.

Human polymorphonuclear leukocytes (PMN's) were prepared from a 10 ml sample of heparinized blood. The red cells were sedimented in phosphate buffered saline containing 5% dextran, and the leukocyte rich supernatant removed and washed in heparin-saline by repeated centrifugation. The concentrated leukocytes were then suspended in gelatine-Hanks' salt solution and their concentration adjusted by hemocytometer counting to 1–2×10$^7$ PMN's/ml.

Piliated phase variant gonococci, heterologous strain F62, was grown on solid typing media for 18 hr at 6.5° C. in 5.6% CO$_2$ and air, the bacteria were harvested with a bent glass rod into Hanks' salt solution and gelatine, and the cell concentration adjusted by nephelometry to 1–2×10$^7$ microorganisms/ml.

sion was washed by centrifugation in Hanks' solution with gelatine, the cell pellet resuspended in Hanks' solution with 10% serum and the reactants were incubated at 37° C. At 0, 30, 60, 90 and 120 min aliquots were removed and intracellular killing stopped by the addition of ice-cold Hanks' solution. The PMN's were then harvested by centrifugation and lysed by the addition of ice-cold distilled water containing 0.1% BSA. Serial ten-fold dilutions in saline were used to determine the number of viable bacteria.

The results are shown in Table 2 as percent of surviving bacteria at 120 min compared to a control sample containing pre-immune antisera.

TABLE 2

| | Bactericidal Activity of Anti-Peptide Sera and Human Polymorphonuclear Leukocytes Surviving Bacteria/Control Survivors × 100 | | | | | | | |
|---|---|---|---|---|---|---|---|---|
| | Anti-Sera Against Conjugates with | | | | | | | |
| Serum Dilution | Constant Region Peptides | | | | Variable Region Peptides | | | |
| | 21–35 | 41–50 | 48–60 | 69–84 | 107–121 | 121–134 | 135–151 | 151–159 |
| 1:10 | 15.6 | 8.6 | 5.1 | 4.6 | 12.4 | 78–1 | 22–4 | 48.8 |
| 1:25 | 33.8 | 14.8 | 11.3 | 8.2 | 28.9 | 94.6 | 32.6 | 63.2 |
| 1:50 | 98.6 | 34.2 | 28.7 | 18.6 | 86.4 | 100 | 48.8 | 89.1 |
| 1:100 | 100 | 81.3 | 62.8 | 58.4 | 100 | 100 | 69.1 | 100 |
| 1:200 | 100 | 100 | 88.1 | 76.3 | 100 | 100 | 88.2 | 100 |

The results show anti-sera raised against conjugates of peptides substantially equivalent to positions 41–50, 48–60, 69–84, and 135–151 to have high titers of opsonic activity; those raised against conjugates substantially equivalent to positions 21–35, 107–121, and 151–159 have lower titers but are opsonic; that raised against conjugates substantially equivalent to positions 121–134 had little opsonic activity.

We claim

1. A vaccine protective against gonorrhea which comprises an effectively protective amount of a peptide wherein the only antigenic determinant is an amino acid sequence that corresponds to residues 21–35, 48–60, 107–121, 135–151 or 151–159 inclusive of *N. gonorrhoeae* MS11(Tr) pilin linked to a substantially antigenically neutral carrier.

2. The vaccine of claim 1 wherein the amino acid sequence which corresponds to residues 21–35, or 48–60 or to residues 151–159, wherein the N-terminal Cys is deleted from the amino acid sequence which corresponds ro residues 151–159, further contains a Cys residue or a Gly-Cys dipiptide at its C terminus.

3. A vaccine protective against gonorrhea which comprises an effectively protective amount of a peptide wherein the only antigenic determinant is an amino acid sequence selected from the group consisting of
(a) Leu-Pro-Ala-Tyr-Gln-Asp-Tyr-Thr-Ala-Arg-Ala-Gln-Val-Ser-Glu;
(b) Thr-Glu-Tyr-Tyr-Leu-Asn-His-Gly-Lys-Trp-Pro-Glu-Asn;
(c) Ser-Leu-Trp-Ala-Arg-Arg-Glu-Asn-Gly-Ser-Val-Lys-Trp-Phe-Cys;
(d) Asp-Als-Lys-Asp-Gly-Lys-Glu-Ile-Asp-Thr-Lys-His-Leu-Pro-Ser-Thr-Cys; and
(e) Cys-Arg-Asp-Lys-Ala-Ser-Asp-Ala-Lys
said peptide linked to substantially antigenically neutral carrier.

4. The vaccine of claim 3, wherein each sequency of a or b, or of e, wherein the N-terminal Cys is deleted from e, further includes a C-terminal Cys residue or C-terminal Gly-Cys residues.

5. The vaccine of claim 3, wherein the peptide has sequence (a).

6. The vaccine of claim 3, wherein the peptide has sequence (b).

7. The vaccine of claim 3, wherein the peptide has sequence (c).

8. The vaccine of claim 3, wherein the peptide has sequence (d).

9. The vaccine of claim 3, wherein the peptide has sequence (e).

10. A peptide in substantially pure form which comprises as the sole antigenic determinant an amino acid sequence selected from the group consisting of
(a) Leu-Pro-Ala-Tyr-Gln-Asp-Tyr-Thr-Ala-Arg-Ala-Gln-Val-Ser-Glu;
(b) Thr-Glu-Tyr-Tyr-Leu-Asn-His-Gly-Lys-Trp-Pro-Gly-Asn;
(c) Ser-Leu-Trp-Ala-Arg-Arg-Glu-Asn-Gly-Ser-Val-Lys-Trp-Phe-Cys;
(d) Asp-Ala-Lys-Asp-Gly-Lys-Glu-Ile-Asp-Thr-Lys-His-Leu-Pro-Ser-Thr-Cys; and
(e) Cys-Arg-Asp-Lys-Ala-Ser-Asp-Ala-Lys.

11. The peptide of claim 10, wherein each sequence of a or b, or of e wherein the N-terminal Cys is deleted from e, further includes a C-terminal Cys residue or C-terminal Gly-Cys residue.

12. The peptide of claim 10, which has sequence (a).
13. The peptide of claim 10, which has sequence (b).
14. The peptide of claim 10, which has sequence (c).
15. The peptide of claim 10, which has sequence (d).
16. The peptide of claim 10, which has sequence (e).

* * * * *